United States Patent [19]

Chylewski et al.

[11] 4,138,256
[45] Feb. 6, 1979

[54] METHOD OF PROCESSING PHOTOGRAPHIC SILVER DYE BLEACH MATERIALS

[75] Inventors: Christoph Chylewski; Gérald Jan, both of Marly; Roland Kurzen; Max Meier, both of St. Antoni; Matthias Schellenberg, Marly, all of Switzerland

[73] Assignee: Ciba-Geigy AG, Basel, Switzerland

[21] Appl. No.: 740,710

[22] Filed: Nov. 11, 1976

[30] Foreign Application Priority Data

Nov. 17, 1975 [CH] Switzerland .................. 14861/75

[51] Int. Cl.$^2$ .................. G03C 7/00; G03C 5/24; G03C 5/30; G03C 5/32

[52] U.S. Cl. .................. 96/53; 96/48 R; 96/66 R; 96/60 BF

[58] Field of Search .................. 96/29 R, 60 R, 66 R, 96/60 BF, 59, 107, 108, 109, 53

[56] References Cited

U.S. PATENT DOCUMENTS

| 3,297,446 | 1/1967 | Dunn | 96/107 |
| 3,442,653 | 5/1969 | Dunn | 96/108 |
| 3,578,449 | 5/1971 | Bloom | 96/66 R X |
| 3,594,169 | 7/1971 | Bloom | 96/61 R X |
| 3,640,713 | 2/1972 | Buckler et al. | 96/29 R |
| 3,716,362 | 2/1973 | Meier | 96/53 X |
| 3,954,473 | 5/1976 | Lambert | 96/60 R |
| 3,957,516 | 5/1976 | Schellenberg et al. | 96/53 |
| 4,003,746 | 1/1977 | Bigelow | 96/109 |

Primary Examiner—Edward C. Kimlin
Assistant Examiner—Alfonso T. Suro Picó
Attorney, Agent, or Firm—Sprung, Felfe, Horn, Lynch & Kramer

[57] ABSTRACT

A method of processing photographic silver dye bleach materials which have been exposed imagewise is provided. The process steps are (1) silver developing, (2) dye bleaching, (3) silver bleaching and (4) fixing. The treatment baths for the process steps (2), (3) and (4), or the combined treatment baths useful for process step (3) with at least one the process steps (2) or (4) contain water-soluble tertiary phosphines as silver ligands. These phosphines effect an acceleration of the dye and silver bleaching and they are further suitable stabilizers and optionally antioxidants which yield stable treatment baths.

14 Claims, No Drawings

METHOD OF PROCESSING PHOTOGRAPHIC SILVER DYE BLEACH MATERIALS

The conventional method of processing photographic silver bleach materials, such as that described for example in German Pat. Nos. 1,472,811 and 1,924,723, or also in textbooks (see for example E. Mutter: "Farbenphotographie, Theorie and Praxis," Springer 1967, p. 57), comprises up to 10 steps. However, for individual steps, for example that of colour bleaching, the maintenance of the process conditions for long caused difficulties. For example, in order to attain practical results it was necessary to maintain the temperature and the action time of the baths very exactly. The variability and thus the limited length of use of individual baths, as well as the corrosiveness of the strongly acid dye bleach bath, gave rise to further difficulties.

There has therefore been no lack of attempts to simplify the method of processing and, above all, also to shorten it. These attempts have established that, while maintaining certain conditions which relate both to the material to be processed and to the composition of the treatment baths, it is possible to produce a useful material with the minimum number of the four following process steps:

(1) silver developing (developing the latent image),
(2) dye bleaching (bleaching the image dyes in relation to imagewise developed silver),
(3) silver bleaching (oxidative removal of the residual silver which is not consumed during the colour bleaching),
(4) fixing (removal of the light-sensitive silver compounds which remain at the areas where no image has been produced and which formed during the silver bleaching).

Washing can be performed between these steps; but it is also possible to dispense with intermediate washing procedures under suitable process conditions and only to keep the final washing step. What is in effect a four-step processing method of this kind is described in German Offenlegungsschrift No. 2,530,469; German Offenlegungsschrift No. 2,309,526 discloses that the method can be shortened and speeded up still further by combining the silver bleaching with the fixing step.

Additional possibilities of shortening the processing method arise from a combination of steps (2) and (3), i.e. the dye bleaching and silver bleaching. German Offenlegungsschrift No. 2,448,433 discloses such a processing method, which, provided the final washing step is left out of account, comprises only three steps, namely (1) the silver development, (2) and (3) a combined dye and silver bleaching bath, and (4) the mixing bath.

Finally German Pat. No. 735,672 teaches a silver bleach method in which even process steps (2), (3) and (4) have been combined in a single bath, so that the entire processing method comprises only two steps. However, in actual practice this method encounters considerable difficulties and it has therefore never been possible to develop it to final fruition.

In analogy to other processes of silver halide photography, in certain process steps of the silver dye bleach method so-called silver ligands are also used, i.e. those substances which lower the concentration of free silver ions in the processing solutions by forming stable complexes with these. In particular, the use of complexing agents, such as thiosulphate or thiocyanate ions or also for example thiourea, in the fixing process is known, wherein advantage is taken of the ready solubility of the silver complexes in question in order to remove the light-sensitive silver compounds from the material. As regards the silver dye bleaching processing, it has long been known to use silver ligands also for process steps (2) and (3), i.e. for the dye bleaching and the silver bleaching, in order to carry out these process steps to give a result which is of practical use. Thus, for example, thiourea, thiosemicarbazide, and halide ions, such as chloride, bromide or iodide ions, are used for this purpose. The ready solubility of the complexes is of secondary importance in these process steps, since the silver complexes do not have to be ultimately removed from the material until the subsequent fixing.

Under specific conditions and for special ends, small amounts of silver ligands are also used in process step (1), the silver developing. Consequently, with silver dye bleach materials which contain in individual layers iodide-free silver halide, and adjacent to these a layer of nuclei, it is possible to produce specific masking effects by using a developer which contains a silver ligand.

The present invention is based on the observation that, when processing silver dye bleach materials, certain tertiary phosphines can be used with advantage as silver ligands in process steps (2), (3) and (4), in particular in steps (2) and (3). If they are added to the treatment baths, preferably in small amounts, for example from 1 to 20 g per liter, they effect a suprising intensification of the reactions, in particular an acceleration of the dye bleaching and of the silver bleaching. Such an advantageous effect is observed both when process steps (2) and (3) are carried out separately and when they are preferably combined to a joint treatment (2) + (3). Further combined treatment baths can also be used for process steps (3) + (4) or also (2) + (3) + (4).

Accordingly, the present invention provides a method of processing photographic silver dye bleaching materials involving the process steps (1) silver developing,
(2) dye bleaching,
(3) silver bleaching,
(4) fixing, it being possible to combine process step (3) with at least one of the process steps (2) and (4) in a single treatment step, wherein a water-soluble phosphine of the formula

is used as silver ligand, wherein W is a radical of the formula $-C_rH_{2r}CN$ or $-C_rH_{2r}NO_2$, in which r is an integer from 1 to 25, a substituted or unsubstituted aryl radical or a heterocyclic radical, X is an optionally further substituted alkyl group and Y is a radical of the formula

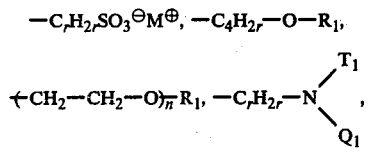

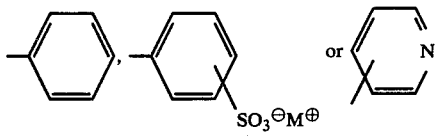

wherein n is an integer from 1 to 5, r is an integer from 1 to 25 and $M^{\oplus}$ is a cation, each of $R_1$, $Q_1$ and $T_1$ is independently a hydrogen atom or an alkyl group of 1 to 4 carbon atoms, $Q_1$ and $T_1$ together with n can also form one of the radicals of the formulae

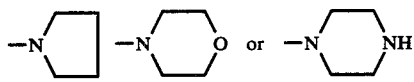

and X and Y together are —CH$_2$—CH$_2$—NR$_1$—CH$_2$—CH$_2$—, wherein R$_1$ is a hydrogen atom or an alkyl group of 1 to 4 carbon atoms.

The water-soluble phosphine of formula (1) used as silver ligand can form with the Ag$^{\oplus}$ ion at least a 2:1 complex (AgL$_2^{\oplus}$) whose gross stability constant $\beta_2 =$ [AgL$_2^{\oplus}$]/[Ag$^{\oplus}$][L]$^2$ is at least $10^{13}$, but is preferably in the region of $10^{16}$ to $10^{18}$. The corresponding phosphonium ion has in general a pK$_a$ value of less than 5, preferably less than 3. However, this feature imposes no limitation on the performance of the method of the invention.

The cation $M^{\oplus}$ can be for example $H^{\oplus}$, $Na^{\oplus}$, $K^{\oplus}$, $(NH_4)^{\oplus}$, (amine)$^{\oplus}$, optionally also $Ca^{\oplus\oplus}$ or $Mg^{\oplus\oplus}$ [$=M^{\oplus}M^{\oplus}$].

$Q_1$ is a hydrogen atom or an alkyl group of 1 to 4 carbon atoms, for example methyl, ethyl, iso-propyl, n-butyl or tert. butyl, and $Q_1$ together with $T_1$ and N can also form one of the cyclic radicals

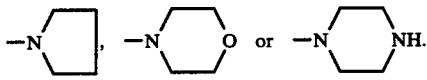

The substituent $R_1$ represents a hydrogen atom or an alkyl group of 1 to 4 carbon atoms. Suitable alkyl groups are those mentioned above in the definition of $Q_1$.

$T_1$ is a hydrogen atom or an alkyl group of 1 to 4 carbon atoms (cf. the definition of $Q_1$) and together with $Q_1$ and N can also form one of the cyclic radicals

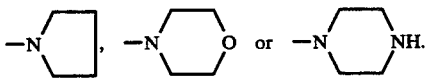

W is one of the radicals of the formulae —C$_r$H$_{2r}$—CN and —C$_r$H$_{2r}$—NO$_2$ with preferably unbranched carbon chain, wherein r is an integer from 1 to 25, an aryl radical, in particular phenyl, which is optionally further substituted by halogen atoms, in particular chlorine or bromine atoms by alkyl, alkoxy or sulfonic acid radicals, or W is a heterocyclic radical.

Preferred phosphines have the following formulae (2) to (6):

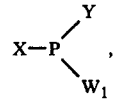

wherein X and Y have the indicated meanings and $W_1$ is a pyridine, pyrazine or triazine radical or a radical of the formulae —CH$_2$—CH$_2$—CN, —CH$_2$—CH$_2$—NO$_2$,

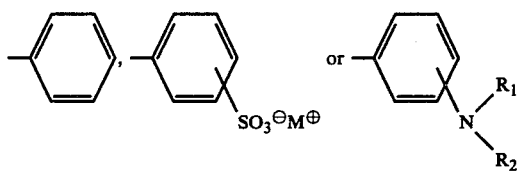

wherein $M^{\oplus}$ is a cation and each of $R_1$ and $R_2$ is independently a hydrogen atom or an alkyl group of 1 to 4 carbon atoms;

wherein $W_1$ and Y have the indicated meanings and $X_1$ is

—(CH$_2$—CH$_2$O)$_n$—R$_1$, —alkyl—SO$_3^{\ominus}$M$^{\oplus}$, —alkyl—SO$_2$—U,
—alkyl—PO$_3^{\ominus\ominus}$M$^{\oplus}$M$^{\oplus}$, —alkyl—CO—O—R$_1$,

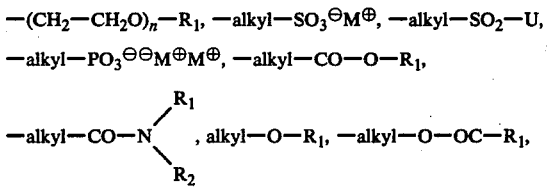

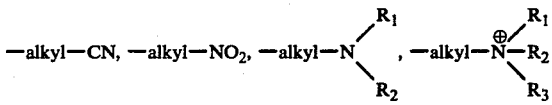

or alkyl-halogen, wherein the alkyl moiety contains 1 to 15 carbon atoms, $M^{\oplus}$ is a cation, each of $R_1$, $R_2$ and $R_3$ independently is a hydrogen atom or an alkyl group of 1 to 4 carbon atoms, U is an alkyl group of 1 to 4 carbon atoms and n is an integer from 1 to 5, and $X_1$ and Y together can be —CH$_2$—CH$_2$—NR$_1$—CH$_2$—CH$_2$—, wherein R$_1$ has the indicated meaning;

wherein $W_1$ and $X_1$ have the indicated meanings and $Y_1$ is

—C$_{r_1}$H$_{2r_1}$SO$_3^{\ominus}$M$^{\oplus}$, —C$_{r_1}$H$_{2r_1}$—O—R$_1$, —(CH$_2$—CH$_2$—O)$_{\overline{n}}$R$_1$,

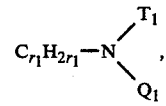
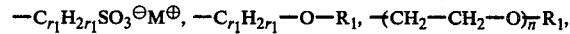

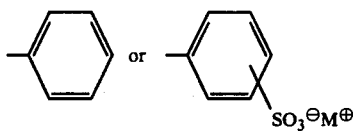

wherein n is an integer from 1 to 5, $r_1$ is an integer from 1 to 15 and $M^\oplus$ is a cation, and each of $R_1$, $Q_1$ and $T_1$ independently is a hydrogen atom or an alkyl group of 1 to 4 carbon atoms, $Q_1$ and $T_1$ together with N can form a radical of the formula

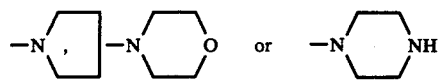

and $X_1$ and $Y_2$ together can be $-CH_2-CH_2-NR_1-CH_2-CH_2-$, wherein $R_1$ has the indicated meaning;

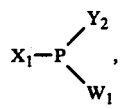 (5)

wherein $W_1$ and $X_1$ have the indicated meanings and $Y_2$ is

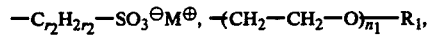

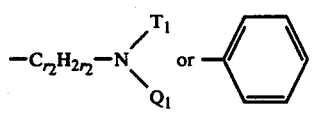

wherein $n_1$ is an integer from 1 to 3, $r_2$ is an integer from 1 to 4 and $M^\oplus$ is a cation, each of $R_1$, $Q_1$ and $T_1$ is independently a hydrogen atom or an alkyl group of 1 to 4 carbon atoms and $Q_1$ and $T_1$ together with N can form a radical of the formula

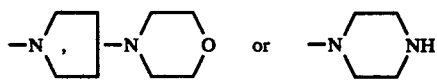

and $X_1$ and $Y_2$ together can be $-CH_2-CH_2-NR_1-CH_2-CH_2-$, wherein $R_1$ has the indicated meaning;

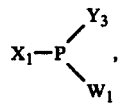 (6)

wherein $W_1$ and $X_1$ have the indicated meanings and $Y_3$ is

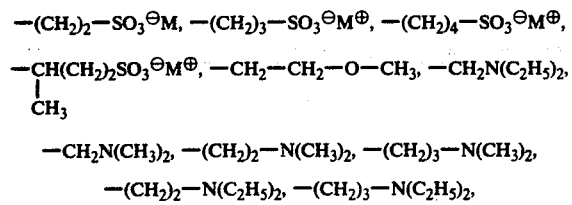

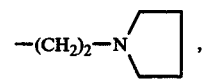

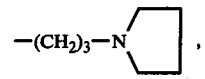

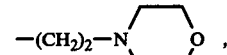

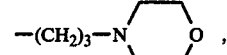

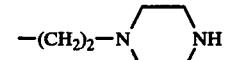

or

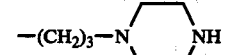

wherein $M^\oplus$ is a cation and $X_1$ and $Y_3$ together can be $-CH_2-CH_2-NR_1-CH_2-CH_2-$ wherein $R_1$ has the indicated meaning.

Particularly suitable phosphines are also those of the formulae

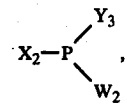 (7)

wherein $Y_3$ has the indicated meaning, $W_2$ is

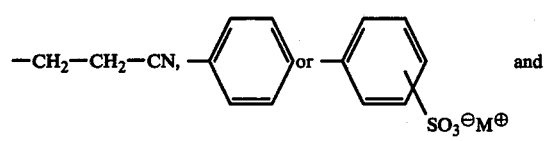

$X_2$ is $-$alkyl$-SO_3^\ominus M^\oplus$, $-$alkyl$-CO-O-R_1$, $-$alkyl$-CO-N\begin{smallmatrix}R_1\\R_2\end{smallmatrix}$, $-(CH_2-CH_2O)_nR_1$, $-$alkyl$-O-R_1$, $-$alkyl$-CN$ or $-$alkyl$-$halogen, wherein each of $R_1$ and $R_2$ is independently a hydrogen atom or an alkyl group of 1 to 4 carbon atoms, alkyl is an alkylene group of 1 to 4 carbon atoms, n is an integer from 1 to 5, $M^\oplus$ is a cation and halogen is in particular a chlorine or bromine atom, and $X_2$ and $Y_3$ together can be $-CH_2-CH_2-NR_1-CH_2-CH_2-$, wherein $R_1$ has the indicated meaning, and phosphines of the formula

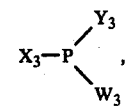 (8)

wherein $Y_3$ has the indicated meaning, $W_3$ is $-CH_2-CH_2-CN$ or

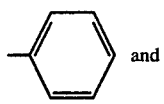 and $X_3$ is $-(CH_2)_k-SO_3^\ominus M^\oplus$, $-(CH_2)_k CN$, $-(CH_2)_{\overline{n_1}} OR_1$,

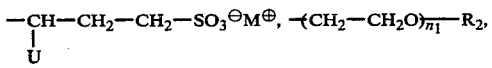

wherein $M^\oplus$ is a cation, U is an alkyl group of 1 to 4 carbon atoms and $n_1$ is an integer from 1 to 3 and k is an integer from 2 to 4, $R_1$ and $R_2$ have the indicated meanings and $X_3$ and $Y_3$ together can be $-(CH_2)_2-N(CH_3)(CH_2)_2-$.

Particularly useful phosphines are also those of the formula

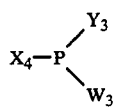 (9)

wherein $W_3$ and $Y_3$ have the indicated meanings and $X_4$ is $-CH_2-CH_2-CN$, $-(CH_2)_2-SO_3^\ominus M^\oplus$, $-(CH_2)_3-SO_3^\ominus M^\oplus$,

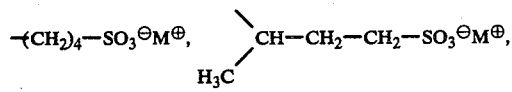

$-(CH_2)_2-O-CH_3$ and $-(CH_2)_2-O-(CH_2)_2-O-CH_3$, wherein $M^\oplus$ is cation and $X_4$ and $X_3$ together can be

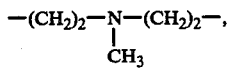

or phosphines of the formula

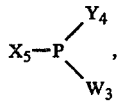 (10)

wherein $W_3$ has the indicated meaning, $Y_4$ is $-(CH_2)_2-SO_3^\ominus M^\oplus$, $-CH_2N(C_2H_5)_2$, $-(CH_2)_3-SO_3^\ominus M^\oplus$, $-(CH_2)_4-SO_3{}^\ominus M^\oplus$ or $-(CH_2)_2-O-CH_3$, $X_5$ $-CH_2-CH_2CN$ or $-(CH_2)_2-O-CH_3$ and $M^\oplus$ is a cation and $X_5$ and $Y_4$ together can be

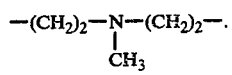

A number of the phosphines of the formulae (1) to (5) are known and those of the formulae (6) to (10) are new. The phosphines can be obtained by methods which are known per se. Suitable methods of obtaining them are described for example by Kosolapoff-Maier in "Organic Phosphorus Compounds," Vol. 1, Chapter 1 (L. Maier), J. Wiley, New York, 1972. Preferred methods are for example the reaction of alkali or alkaline earth alkylphosphides with alkyl halides or the alkylation of tertiary phosphines to give tetra-alkylphosphonium salts and subsequent dealkylation. In this way it is possible to obtain tertiary phosphines with two or three different substituents. Details of this method are to be found in the manufacturing examples. The following phosphines and alkylating agents can be used for example to obtain the phosphines of the formula (1):

Phosphines tris-(2-cyanoethyl)-phosphine, bis-(2-cyanoethyl)-phosphine, (2-cyanoethyl)-phosphine, bis-(2-cyanoethyl)-phenylphosphine, (2-cyanoethyl)-phenyl-phosphine, (2-cyanoethyl)-diphenyl-phosphine, phenylphosphine, diphenylphosphine, tris-(hydroxymethyl)-phosphine, (2-methoxyethyl)-phosphine, bis-(2-methoxyethyl)-phosphine, bis-(2-cyanoethyl)-(2-methoxyethyl)-phosphine, bis-(hydroxymethyl)-phosphine, bis-(2-cyanoethyl)-(hydroxymethyl)-phosphine, bis-(hydroxymethyl)-2-cyanoethyl-phosphine, 2-cyanoethyl-hydroxymethyl-phenylphosphine.

Alkylating agents methyl vinyl sulphone, acrylonitrile, acrylic acid, methyl acrylate, ethyl acrylate, acrylic amide, methyl vinyl ether, 2-chloroethanesulphonic acid, 2-bromoethanesulphonic acid, 2-iodoethanesulphonic acid, 3-chloro-1-propanesulphonic acid, 3-bromo-1-propanesulphonic acid, 3-iodo-1-propanesulphonic acid, 4-chloro-1-butanesulphonic acid, 4-bromo-1-butanesulphonic acid, 4-iodo-1-butanesulphonic acid, propane sultone, butane sultone, 3-methylpropane sultone, 1-chloro-2-methoxyethane, 1-bromo-2-methoxyethane, 1-iodo-2-methoxyethane, (2-bromoethyl)-methylsulphone, (2-chloroethyl)-methylsulphone, (2-chloroethoxy)-1-methoxyethane, (2-bromoethoxy)-1-methoxyethane, (2-iodoethoxy)-1-methoxyethane, (2-iodoethyl)-methylsulphone, bis-N,N-(2-chloroethyl)-N-methylamine, bis-N,N-(2-chloroethyl)-N-ethylamine, bis-N,N-(2-chloroethyl)-N-propylamine, bis-N,N-(2-chloroethyl)-N-isopropylamine, bis-N,N-(2-chloroethyl)-N-isopropylamine, bis-N,N-(2-chloroethyl)-N-butylamine, bis-N,N-(2-chloroethyl)-N-sec. butylamine, bis-N,N-(2-chloroethyl)-N-isobutylamine, bis-N,N-(2-chloroethyl)-N-tert. butylamine, N-(2-chloroethyl)-N,N-dimethylamine, N-(2-chloroethyl)-N,N-diethylamine, N-(3-chloro-1-propyl)-N,N-dimethylamine, N-(3-chloro-1-propyl)-N,N-diethylamine, N-(4-chloro-1-butyl)-N,N-dimethylamine, N-(4-chloro-1-butyl)-N,N-diethylamine, N-(2-chloroethyl)-pyrrolidine, N-(3-chloro-1-propyl)-pyrrolidine, N-(4-chloro-1-butyl)-pyrrolidine, N-(2-chloroethyl)-piperidine, N-(3-chloro-1-propyl)-piperidine, N-(4-chloro-1-butyl)-piperidine, N-(2-chloroethyl)-morpholine, N-(3-chloropropyl)-morpholine, N-(4-chlorobutyl)-morpholine.

The sulphonic acids are ordinarily used in the form of their alkali metal salts.

A number of representative phosphines which can be used in the processing method of the present invention are listed herein below:

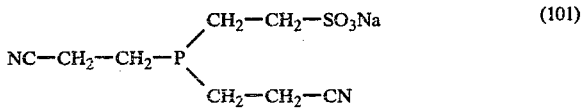 (101)

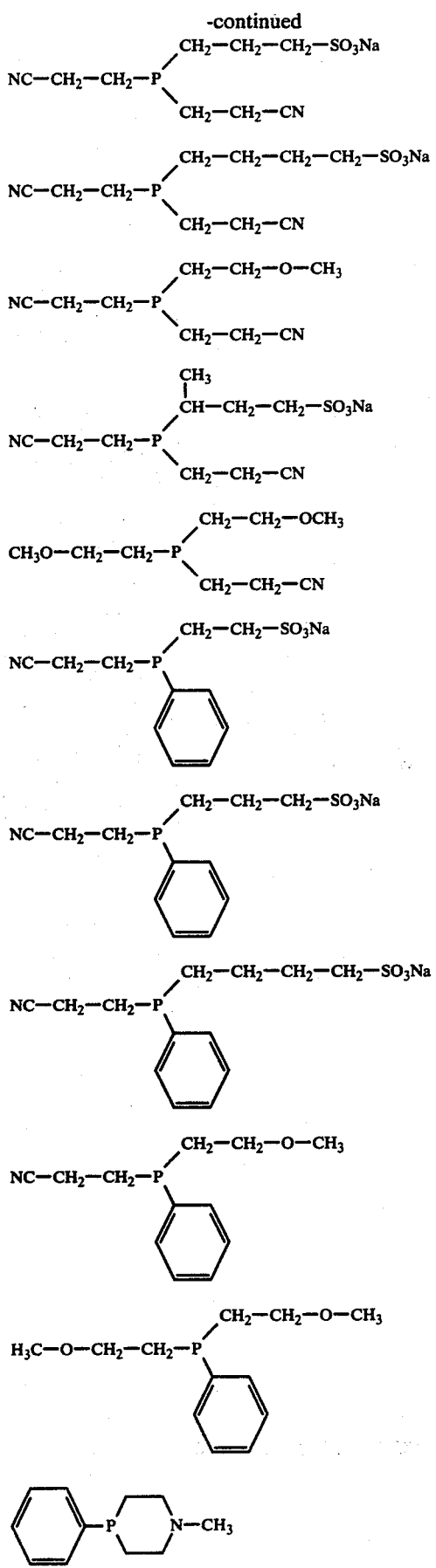

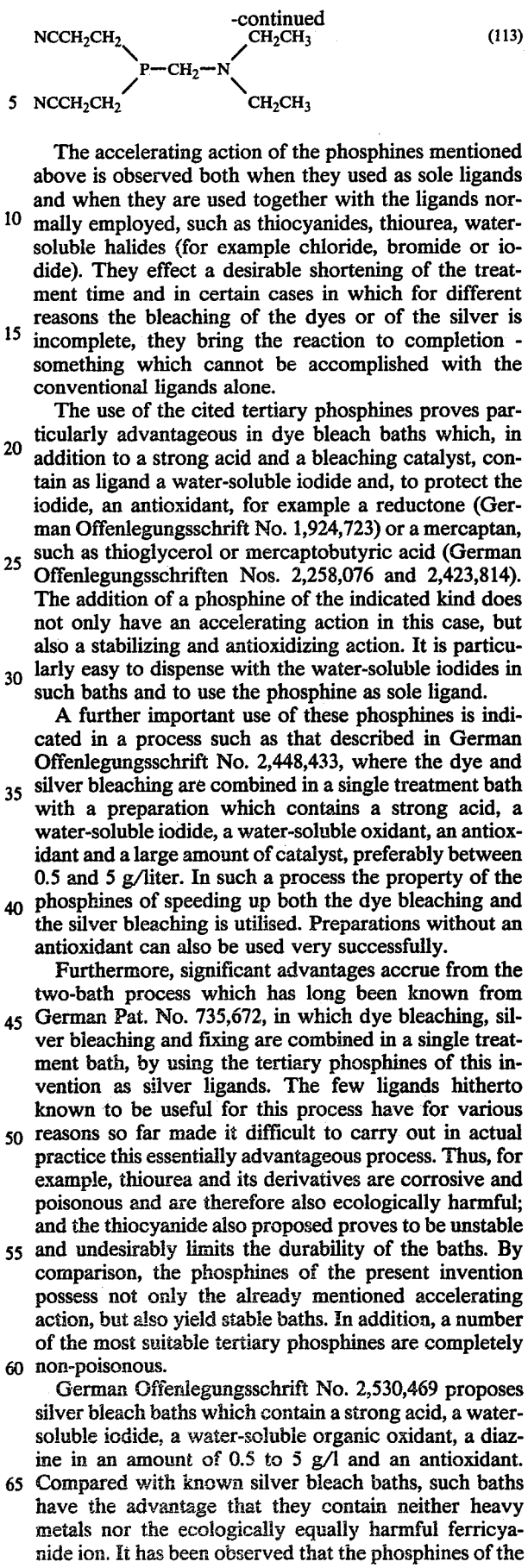

The accelerating action of the phosphines mentioned above is observed both when they used as sole ligands and when they are used together with the ligands normally employed, such as thiocyanides, thiourea, water-soluble halides (for example chloride, bromide or iodide). They effect a desirable shortening of the treatment time and in certain cases in which for different reasons the bleaching of the dyes or of the silver is incomplete, they bring the reaction to completion - something which cannot be accomplished with the conventional ligands alone.

The use of the cited tertiary phosphines proves particularly advantageous in dye bleach baths which, in addition to a strong acid and a bleaching catalyst, contain as ligand a water-soluble iodide and, to protect the iodide, an antioxidant, for example a reductone (German Offenlegungsschrift No. 1,924,723) or a mercaptan, such as thioglycerol or mercaptobutyric acid (German Offenlegungsschriften Nos. 2,258,076 and 2,423,814). The addition of a phosphine of the indicated kind does not only have an accelerating action in this case, but also a stabilizing and antioxidizing action. It is particularly easy to dispense with the water-soluble iodides in such baths and to use the phosphine as sole ligand.

A further important use of these phosphines is indicated in a process such as that described in German Offenlegungsschrift No. 2,448,433, where the dye and silver bleaching are combined in a single treatment bath with a preparation which contains a strong acid, a water-soluble iodide, a water-soluble oxidant, an antioxidant and a large amount of catalyst, preferably between 0.5 and 5 g/liter. In such a process the property of the phosphines of speeding up both the dye bleaching and the silver bleaching is utilised. Preparations without an antioxidant can also be used very successfully.

Furthermore, significant advantages accrue from the two-bath process which has long been known from German Pat. No. 735,672, in which dye bleaching, silver bleaching and fixing are combined in a single treatment bath, by using the tertiary phosphines of this invention as silver ligands. The few ligands hitherto known to be useful for this process have for various reasons so far made it difficult to carry out in actual practice this essentially advantageous process. Thus, for example, thiourea and its derivatives are corrosive and poisonous and are therefore also ecologically harmful; and the thiocyanide also proposed proves to be unstable and undesirably limits the durability of the baths. By comparison, the phosphines of the present invention possess not only the already mentioned accelerating action, but also yield stable baths. In addition, a number of the most suitable tertiary phosphines are completely non-poisonous.

German Offenlegungsschrift No. 2,530,469 proposes silver bleach baths which contain a strong acid, a water-soluble iodide, a water-soluble organic oxidant, a diazine in an amount of 0.5 to 5 g/l and an antioxidant. Compared with known silver bleach baths, such baths have the advantage that they contain neither heavy metals nor the ecologically equally harmful ferricyanide ion. It has been observed that the phosphines of the present invention also exert an accelerating and stabilising action in such baths. As in the dye bleach baths mentioned above, the iodide ion can also be replaced here completely by a phosphine.

A further use of the proposed phosphines comprises bleach fixing baths, for example those which have been proposed for silver dye bleach materials in German Offenlegungsschrift No. 2,309,526. Such baths contain a water-soluble oxidant, for example the sodium salt of 2,4-dinitrobenzenesulphonic acid, and thiourea as silver ligand. The pH is kept at a maximum value of 1 by a strong acid, such as sulphuric acid. It has been observed that the phosphines of the present invention also exhibit an accelerating action in such baths.

A particularly advantageous use of the phosphines of this invention resides in the production of masked positive coloured images by means of the silver dye bleach process, in which a photographic material is used which contains, in each of at least two layers, a dye which can be bleached imagewise and whose absorption maximum corresponds to one of the primary colours red, green and blue, with a silver halide emulsion layer sensitive to a particular spectral region being assigned to each dye, and in this material, (a) a silver halide emulsion layer consisting at least partially of silver iodide is assigned to the dye whose undersired parasitic colour density is to be compensated, (b) in a further layer, at least a second dye whose main colour density corresponds to a parasitic colour density, requiring compensation, of the first dye, and a silver halide emulsion which contains no iodide ions are present, (c) a further layer, which is adjacent to the layer containing the second dye, contains colloidal nuclei which are capable of depositing metallic silver from soluble silver complexes, (d) a separating layer is present between the layer containing the nuclei and the dye layer the parasitic colour density of which is to be compensated, and the silver developing bath with which the material is treated contains a ligand which is able to produce water-soluble silver complexes which are capable of diffusion.

The following Examples 1 to 9 relate to the production of new phosphines and Examples 10 to 15 to the use of the inventive phosphines as silver ligands.

EXAMPLE 1

Bis-(β-cyanoethyl)-sulphoethylphosphine (formula 101)

Phosphonium salt of tris-(2-cyanoethyl)-2-ethylsulphonic acid 19.3 g (0.1 mole) of tris-(2-cyanoethyl)-phosphine, 21.1 g (0.1 mole) of the sodium salt of ethanesulphonic acid and 120 ml of ethylene glycol monomethyl ether are refluxed for 40 hours. The mixture is cooled in ice and the precipitated solid is collected by filtration, washed with a small amount of ethylene glycol monomethyl ether and finally dried in vacuo at 60° C.

Yield: 20 g (66.4% of theory).
Melting point: 253°–258° C. (with decomposition).

Bis-(β-cyanoethyl)-2-sulphoethylphosphine 1.5 g of sodium metal (0.0652 mole) are dissolved in 60 ml of absolute methanol. Then 20 g of the above phosphonium salt (0.0664 mole) and 20 ml of absolute methanol are added. The mixture is refluxed for 2 hours and then cooled, whereupon a white crystalline product precipitates. The batch is filtered and then 120 ml of absolute toluene are added to the filtrate, whereupon further crystals precipitate. The combined crystalline product is dried in vacuo at 60° C.

Yield: 11.7 g (66.4% of theory).
Melting point: 119°–124° C.; content (iodine titre) : 89%.

EXAMPLE 2

Bis-(β-cyanoethyl-3-sulphopropylphosphine, sodium salt (formula 102)

Starting material: tris-(β-cyanoethyl)-phosphine
Manufacture by the method of W. J. Vullo, Ind. Eng. Chem. Prod. Res. Dev. 5, 346 [1966]

Phosphonium salt of tris-(β-cyanoethyl)-3-propylsulphonic acid 15.4 g (0.08 mole) of tris-(β-cyanoethyl)-phosphine and 46 ml of toluene are refluxed for 30 minutes. After addition of 9.84 g (0.08 mole) of propanesultone, the mixture is refluxed for 3 hours and then cooled to 20° C. The precipitated solid is collected by suction filtration and dried in vacuo at 60° C.

Yield: 24.4 g (97.5% of theory)
Melting point: 257°–260° C. (with decomposition).

Bis-(β-cyanoethyl)-3-sulphopropylphosphine (sodium salt)

24.4 g of the above intermediate are dissolved, under nitrogen, in 100 ml of absolute methanol and 1.85 g (0.08 mole) of sodium methylate are added to the solution. The mixture is refluxed for 2 hours and then cooled to 20° C. Upon onset of crystallisation, 120 ml of ethyl ether are added dropwise and the suspension is further stirred for 30 minutes. The precipitated solid is collected by suction filtration, washed with 80 ml of ether and dried in vacuo at 60° C.

Yield: 22.9 g (100%, referred to the intermediate).
Melting point: 125°–130° C. (with decomposition).
Content (iodine titre): 71 to 72%.

EXAMPLE 3

Bis-(β-cyanoethyl)-4-sulpho-1-butylphosphine (formula 103)

Bis-(β-cyanoethyl)-4-sulpho-1-butylphosphonium salt 19.3 g (0.1 mole) of tris-(β-cyanoethyl)-phosphine, 13.6 g (0.1 mole) of butane sultone, 1.5 g (0.01 mole) of sodium iodide and 100 ml of dimethyl formamide are refluxed for 20 hours. The mixture is cooled to 5° C. and precipitated solid is separated, washed with acetone and dried at 60° C. in vacuo.

Yield: 23.5 g (71.4% of theory).
Melting point: 284°–285° C. (with decomposition).

Bis-(β-cyanoethyl)-4-sulpho-1-butylphosphine 16.5 g (0.05 mole) of the above intermediate are added, under nitrogen, to a solution of 1.15 g (0.0 mole) of sodium in 60 ml of absolute methanol. The mixture is refluxed for 5 hours and then cooled to 5° C. Then 150 ml of isopropanol are added and the suspension is further stirred for 30 minutes. The precipitated solid is filtered off with suction, washed with 150 ml of toluene and dried in vacuo at 60° C.

Yield: 13.3 g (89% of theory).
Melting point: 134°–139° C.
Content (iodine titre): 92%.

EXAMPLE 4

Bis-(β-cyanotheyl)-2-methoxyethylphosphine (formula 104)

Tris-(β-cyanoethyl)-2-methoxyethyl-phosphonium iodide 135.2 g (0.7 mole) of tris-(2-cyanoethyl)-phosphine are dissolved, under nitrogen, in 500 ml of boiling acetonitrile and then 130.2 g (0.7 mole) of 1-iodo-2-methoxyethane are added. The mixture is refluxed for 12 hours. After rapid filtration of the hot solution and cooling, the reaction product crystallises out and is collected by suction filtration and dried in vacuo at 60° C.

Yield: 205.8 g (77.5% of theory).
Melting point: 170°–171° C.

Bis-(β-cyanoethyl)-2-methoxyethylphosphine 1.55 g of sodium are dissolved in 100 ml of absolute methanol under an atmosphere of argon and then 26 g (0.0685 mole) of tris-(β-cyanoethyl)-2-methoxyethylphosphonium iodide are added to this solution. The solution is refluxed for 4 hours. After the mixture has been poured into water, extraction is performed with three 40 ml portions of chloroform. The chloroform solution is dried over magnesium sulphate, the solvent is evaporated and the oily residue distilled in a high vacuum.

Yield: 9.65 g (71% of theory).
Boiling point: 146°–147° C. (0.026 mbar).

EXAMPLE 5

Bis-(2-methoxyethyl)-β-cyanoethylphosphine (formula 106)

Bis-(β-cyanoethyl)-2-bis-(2-methoxyethyl-phosphonium iodide

This product is obtained in similar manner to tris-(β-cyanoethyl)-2-methoxyethyl-phosphonium ioxide (Example 4) by alkylating bis-(2-cyanoethyl)-2-methoxyethylphosphine with 1-iodo-2-methoxyethane.

Yield: 96% of theory.
Melting point: 103°–106° C.

Bis-(2-methoxyethyl)-(β-cyanoethyl)-phosphine

This phosphine is obtained in similar manner to bis-(2-cyanoethyl)-2-methoxyethylphosphine (Example 4) from bis-(2-cyanoethyl)-bis-(2-methoxyethyl)-phosphonium iodide.

Yield: 10% of theory.
Boiling point: 103°–104° C. (0.09 Torr).

Example 6

β-Cyanoethyl-phenyl-3-sulphopropylphosphine (formula 108)

Starting product: phenylphosphine
F. Pass & H. Schindlbauer, Monatshefte Chemie 90 148 [1959]

Bis-(β-cyanoethyl)-phenylphosphine

M.M. Rauhut et al., J. Am. Chem. Soc. 81,1106 [1959]

Phosphonium salt of bis-(β-cyanoethyl)-phenyl-3-propyl-1-sulphonic acid 8.5 g (0.039 mole) of bis-(β-cyanoethyl)-phenylphosphine, 20 ml of absolute acetonitrile and 4.76 g (0.039 mole) of propanesultone are refluxed for 16 hours under a nitrogen atmosphere. After evaporation of the solvent, the solid residue is heated for 2 hours with ethyl and then filtered off with suction and dried in vacuo to yield 12 g (79%) of the phosphonium salt. The NMR spectrum is in accord with the expected formula.

(β-Cyanoethyl)-phenyl-3-sulphopropylphosphine (sodium salt)

0.7 g of sodium are dissolved in 40 ml of absolute methanol in an atmosphere of nitrogen. The 12 g of the phosphonium salt of bis-(2-cyanoethyl)-phenyl-(3-propyl-1-sulphonic acid are added and the mixture is refluxed for 12 hours. The solution is cooled and poured into water. The insoluble constituent is filtered off and the water is completely evaporated. The residue is taken up in ether, filtered off with suction, washed once more with ether and dried in vacuo at 70° C.

Yield: 8.5 g (92% of theory).
Melting point: 120° C. (with decomposition).
The NMR spectrum (in dimethyl sulphoxide) accords with the expected formula.

EXAMPLE 7

β-Cyanoethyl-2-methoxyethylphenylphosphine (formula 110)

Bis-(β-cyanoethyl-2-methoxyethyl-phenylphosphonium iodide 8.5 g (0.04 mole) of bis-(β-cyanoethyl)-phenylphosphine are dissolved in 50 ml of absolute acetonitrile in a nitrogen atmosphere. Then 7.71 g (0.04 mole) of 1-iodo-2-methoxyethane are added and the mixture is refluxed for 12 hours. The solvent is distilled off to yield 13.2 g (82% of theory) of the product in the form of a solid, glassy substance.

β-Cyanoethyl-2-methoxyethyl-phenylphosphine

The product is obtained from bis-(2-cyanoethyl)-2-methoxyethyl-phenylphosphonium iodide by reaction with sodium methylate in absolute methanol, in the same way as the end product of Manufacturing Example 4.

Yield: 53% of theory.
Boiling point: 125° C. (0.13 mbar).

EXAMPLE 8

Bis-(2-methoxyethyl)-phenylphosphine (formula 111)

39.2 g (1.7 mole) of sodium are finely dispersed in 500 ml of boiling toluene, using a vibrator, in an argon atmosphere. Without cooling, a solution of 71.6 g (0.4 mole) of phenyl-dichlorophosphine in 150 ml of dry toluene is slowly added dropwise. The mixture is refluxed for a further 5 hours. Then 85 g (0.9 mole) of 1-chloro-2-methoxyethane are slowly added dropwise, in the course of which the mixture reacts vigorously. The batch is thereafter refluxed for a further 2 hours. After the batch has cooled, 150 ml of water are added dropwise and the phases are separated. The aqueous solution is extracted a second time with 50 ml of toluene and both toluene solutions are combined. After drying the combined extracts over magnesium sulphate the toluene is evaporated and the residue is distilled in a high vacuum in an atmosphere of argon.

Boiling point: 85°–90° C. (0.39 bar).
Yield: 30.9 g (34% of theory).

EXAMPLE 9

N-Methyl-p-phenyl-perhydro-1,4-azaphosphorane (formula 112)

A solution of phenylmagnesium bromide is prepared from 2.7 g (0.11 mole) of magnesium and 15.7 g of bromobenzene in a total amount of 110 ml of dry tetrahydrofurane. To the cooled solution are added dropwise 5.5 g (0.05 mole) of phenylphosphine in 40 ml of absolute benzene. The mixture is refluxed for 2 hours and cooled again to 30° C. Then 7.8 g of methyl-bis(2-chloroethyl)-amine in 40 ml of dry benzene are added dropwise. The batch is subsequently stirred for 12 hours at room temperature and then refluxed once more for 2 hours. After the batch has cooled, 100 ml of water are added and the phases are separated. After repeated extraction of the aqueous phase with benzene, the solutions are combined and the solvent is evaporated. The oily residue is distilled in vacuo in an argon atmosphere.

Boiling point: 146° C. (11 mbar).

Yield: 3.2 g.

Control of the constitution by NMR, IR and mass spectra.

EXAMPLE 10

A photographic material for the silver dye bleach process is produced on a pigmented cellulose acetate carrier using the cyan image dye of the formula

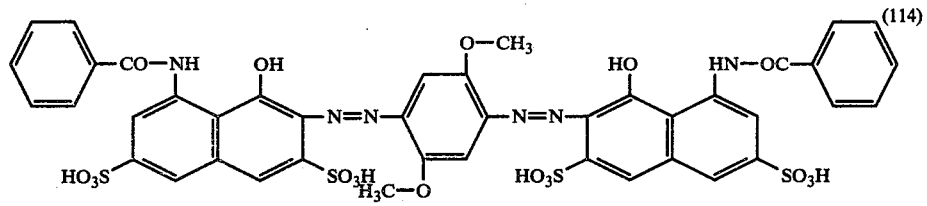

in the red-sensitised bottom layer, the magenta dye of the formula

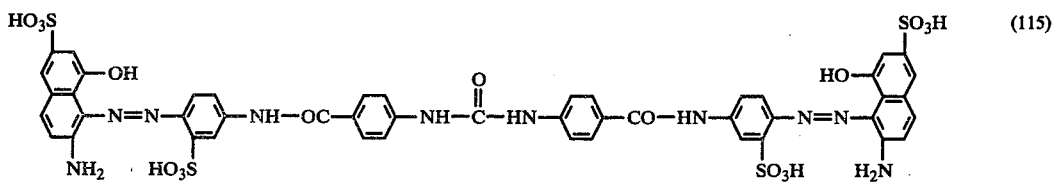

in a green-sensitised layer above this, and the yellow dye of the formula

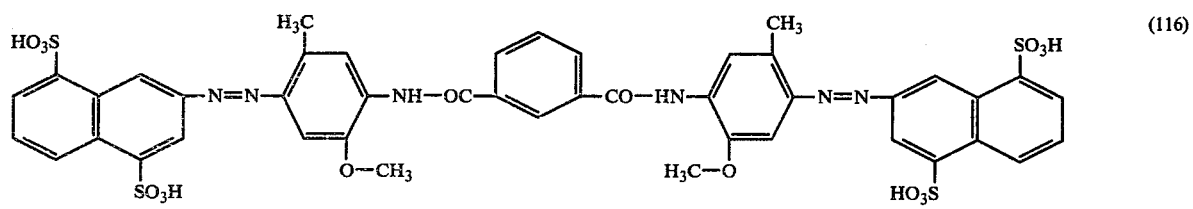

in a blue-sensitive layer above the magenta layer.

The photographic material used is made up as follows (compare German Offenlegungsschriften Nos. 2,036,918 and 2,132,836):

gelatine protective layer
blue-sensitive iodide-free AgBr emulsion
yellow dyestuff (116) + blue-sensitive, iodide-free AgBr emulsion
yellow filter: yellow Ag hydrosol (40 mg/m$^2$)
green-sensitive AgBr/AgI emulsion
magenta dyestuff (115) + green-sensitive AgBr/AgI emulsion
intermediate layer (gelatine)
cyan dyestuff (114) + red-sensitive AgBr/AgI emulsion
red-sensitive AgBr/AgI emulsion
cellulose triacetate carrier, opaque white
backing layer, gelatine The emulsion layers containing iodide contain crystals with 2.6 mol % of silver iodide and 97.4 mol % of silver bromide. The image dyes are used in such a concentration that the reflection density of each is 2.0. The total silver content of the material is 2.0 g/m$^2$, and the overall thickness of the photographic layers is 22μ.

A colour transparency is copied onto this material in an enlarger. The exposed material is processed in accordance with the following instructions. The processing temperature is 24° C.

| 1. Silver developer bath | 3 | minutes |
|---|---|---|
| sodium polyphosphate | 1 | g/l |
| potassium hydroxide (85%) | 27 | g/l |
| boric acid | 16 | g/l |
| potassium metabisulphite | 18 | g/l |
| 1-phenyl-3-pyrazolidone | 0.3 | g/l |
| hydroquinone | 10 | g/l |
| ascorbic acid | 10 | g/l |
| benzotriazole | 0.3 | g/l |
| potassium bromide | 2 | g/l |
| 2. Bleach bath | 5 | minutes |
| sulphamic acid | 140 | g/l |
| sodium-3-nitrobenzenesulphonate | 6 | g/l |
| 4-mercaptobutyric acid | 1 | ml/l |
| potassium iodide | 6 | g/l |
| 2,3,6-trimethylquinoxaline | 2 | g/l |
| 3. Washing | 2 | minutes |
| 4. Fixing bath | 4 | minutes |
| ammonium thiosulphate | 250 | g/l |
| potassium metabisulphite | 50 | g/l |
| potassium hydroxide (85%) | 20 | g/l |
| 5. Washing | 6 | minutes |

The positive reproduction of the original is obtained after a total processing time of 20 minutes.

By using instead of the above bleaching bath one of the composition:

| sulphamic acid | 140 | g/l |
|---|---|---|
| sodium m-nitrobenzenesulphonate | 6 | g/l |
| 2,3,6-trimethylquinoxaline | 2 | g/l |
| potassium iodide | 6 | g/l |
| 4-mercaptobutyric acid | 1 | ml/l |
| bis-($\beta$-cyanoethyl)-sulphoethylphosphine (101) (sodium salt) | 2.5 | g/l | the same result is obtained and the bleaching time is reduced to 3 minutes.

EXAMPLE 11

The same photographic material is used as in Example 10, but using a silver developing bath of the following composition:

| sodium polyphosphate | 1 | g/l |
|---|---|---|
| potassium hydroxide (85%) | 27 | g/l |
| boric acid | 21 | g/l |
| potassium metabisulphite | 18 | g/l |
| 1-phenyl-3-pyrazolidone | 0.3 | g/l |
| hydroquinone | 5 | g/l |
| ascorbic acid | 10 | g/l |
| benztriazole | 0.6 | g/l |
| potassium bromide | 2 | g/l |
| sodium thiosulphate | 1.5 | g/l |

Baths of the same composition as that described in Example 10 are used for the other baths. It is observed that in a bath without the addition of tertiary phosphine the silver is no longer completely bleached out, but leaves a grey fog on the finished processed image.

If, however, 2.5 g/l of bis-($\beta$-cyanoethyl)-sulphopropylphosphine (102) are added to the bleaching bath, then the silver is completely bleached out and the bleaching time is simultaneously reduced. The masking affect obtained by adding sodium thiosulphate to the developer is fully retained and, compared with the images prepared in accordance with Example 10, brilliant saturated blue shades and also at the same time saturated yellow and green shades are obtained. The same result is obtained by using 9 g/l of diphenyl-sulphopropylphosphine instead of bis-($\beta$-cyanoethyl)-sulphopropylphosphine.

EXAMPLE 12

A colour transparency is copied in an enlarger onto the material described in Example 10. Processing is effected using a bath sequence in which the silver developing, dye bleaching, silver bleaching and fixing are carried out in separate successive treatments:

| 1. Silver developing: 6 minutes | | |
|---|---|---|
| sodium polyphosphate | 1 | g/l |
| sodium sulphite, anhydrous | 50 | g/l |
| hydroquinone | 5 | g/l |
| sodium metaborate | 15 | g/l |
| 1-phenyl-3-pyrazolidone | 0.3 | g/l |
| potassium bromide | 3 | g/l |
| benzotriazole. | 0.2 | g/l |
| 2. Washing: 5 minutes | | |
| 3. Dye bleaching: 7 minutes | | |
| water | 800 | ml |
| sulphuric acid (95%) | 14 | ml |
| ascorbic acid | 1 | g |
| potassium iodide | 30 | g |
| 2,3-dimethyl-5-amino-6-methoxy-quinoxaline | 0.08 | g |
| bulked with water to | 1000 | ml |
| 4. Washing: 3 minutes | | |
| 5. Silver bleaching: 3 minutes | | |
| water | 800 | ml |
| sulphuric acid (96%) | 20 | ml |
| 2,4-dinitrobenzenesulphonic acid, sodium salt | 10 | g |
| ascorbic acid | 1 | g |
| potassium iodide | 6 | g |
| ammonium chloride | 20 | g |
| 2,3,6-trimethylquinoxaline | 0.5 | g |
| bulked with water to | 1000 | ml |
| 6. Washing: 3 minutes | | |
| 7. Fixing: 7 minutes | | |
| ammonium thiosulphate | 200 | g/l |
| sodium sulphite, anhydrous | 20 | g/l |
| 8. Washing: 8 minutes | | |

The above silver bleaching bath has the advantage of containing neither heavy metal nor cyanide ions, both of which cause effluent pollution. The bleaching time can be reduced to 1 minute by adding bis-($\beta$-cyanoethyl)-sulphopropylphosphine (102) to this bleaching bath in an amount of 5 g/l. In both cases a true coloured positive copy of the original is obtained. Instead of bis-($\beta$-cyanoethyl)-sulphopropylphosphine (102) it is also possible to use with similar effect bis-($\beta$-cyanoethyl)sulphoethylphosphine (101) or cyanoethyl-phenyl-sulphopropylphosphine (108) or the compound of the formula (112).

EXAMPLE 13

A silver dye bleach material suitable for rapid processing in automatic self-protrait machines is prepared as follows:

Three colour layers are applied superimposed to a paper carrier which is laminated on both sides with polyethylene. The material contains in the bottom layer the cyan dye of the formula

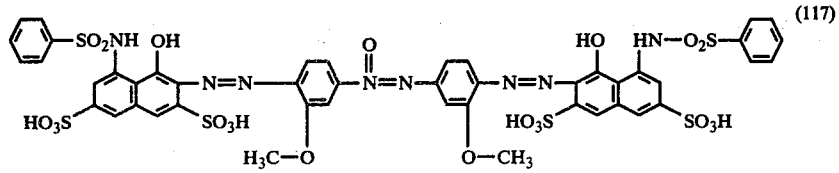

in the green-sensitive layer above it the magenta image dye of the formula (115) and in the top blue-sensitive layer the yellow image dye of the formula (116).

The image dyes are incorporated in a reflectance density of D = 2.0. The colour layers containing a total of 0.8 Ag/m² are separated by gelatine layers, the total thickness being 15μ.

This material is exposed by flashlight in a conventional automatic self-portrait machine and thereafter developed in the processing part of the machine. Fourteen tanks each containing 2.5 liters are available for holding the solutions. The immersion time per tank, including transport, is 20 seconds. The exposed material passes through the following baths at a bath temperature of 35° C:

| Twice, silver developing bath | | | |
|---|---|---|---|
| Composition | | | |
| sodium polyphosphate | 1 | g/l | |
| sodium sulphite, anhydrous | 60 | g/l | |
| hydroquinone | 10 | g/l | |
| sodium metaborate | 20 | g/l | |
| sodium hydroxide | 3 | g/l | |
| 1-phenyl-3-pyrazolidone | 0.4 | g/l | |
| potassium bromide | 1.5 | g/l | |
| benzotriazole | 0.2 | g/l | |
| 2,3-bis-(hydroxymethyl)-6,7-dimethoxy-quinoxaline | 0.2 | g/l | |
| Passage time | | | 40 seconds |
| Twice, dye bleach bath | | | |
| Composition | | | |
| sulphuric acid (96%) | 20 | ml/l | |
| sodium hypophosphite | 2 | g/l | |
| potassium iodide | 20 | g/l | |
| 2,3-bis-(hydroxymethyl)-6,7-dimethoxy-quinoxaline | 80 | mg/l | |
| Passage time | | | 40 seconds |
| Twice, bleach-fixing bath | | | |
| Composition | | | |
| sulphuric acid (96%) | 20 | ml/l | |
| sodium salt of 2,4-dinitrobenzene-sulphonic acid | 70 | g/l | |
| thiourea | 80 | g/l | |
| Passage time | | | 40 seconds |
| 3 times, silver halide fixing bath | | | |
| Composition | | | |
| ammonium thiosulphate, 98/100 | 150 | g/l | |
| sodium sulphate, anhydrous | 30 | g/l | |
| sodium bisulphite | 10 | g/l | |
| Passage time | | | 60 seconds |
| 5 times, washing bath | | | |
| Passage time | | | 100 seconds |
| Total processing time | | | 280 seconds (= 4 minutes 40 seconds) |

By adding 5 g/l of bis-(β-cyanoethyl)-methoxyethylphosphine (104) or of bis-(β-cyanoethyl)-sulphopropylphosphine (102) both to the dye bleach bath and to the bleach fixing bath, the treatment time in both baths can be reduced by half and the result will in other respects be the same.

EXAMPLE 14

This Example illustrates the use of the phosphines of the present invention in a two-bath process, in which the process steps dye bleaching (2), silver bleaching (3) and fixing (4) are combined in a single treatment bath.

In an enlarger, the copy of a colour transparency is prepared on the photographic material used in Example 13 with 3 layers which contain dye and emulsion and each of which is separated by an intermediate layer of gelatine. The exposed material is processed in the following bath sequence at a temperature of 22° C.:

| | | |
|---|---|---|
| sodium polyphosphate | 1 | g/l |
| sodium sulphite, anhydrous | 50 | g/l |
| hydroquinone | 5 | g/l |
| sodium metaborate | 15 | g/l |
| 1-phenyl-3-pyrazolidone | 0.3 | g/l |
| potassium bromide | 3 | g/l |
| benzotriazole | 0.2 | g/l |
| 2. Combined dye-silver-bleach-fixing bath | | |
| Bis-(β-cyanoethyl)-methoxyethylphosphine (10 × 4) | 20 | g/l |
| 2,3-dimethyl-6-methoxyquinoxaline | 3 | g/l |
| sodium 3-nitrobenzenesulphonate | 5 | g/l |
| sulphuric acid (96%) | 30 | ml/l |

After a two minute treatment in this bath, a finished, bleached and fixed positive image of the original is obtained, which only needs to be washed. Instead of the phosphine used in the bleaching bath, it is also possible to use the same amount of bis-(β-cyanoethyl)-sulphoethylphosphine (101) or phenyl-(β-cyanoethyl)-sulphopropylphosphine (108) to obtain the same effect. The treatment time in the combined bleaching and fixing bath can even be reduced to one minute by using a bath of the following composition:

| | |
|---|---|
| bis-(β-cyanoethyl)-sulphopropylphosphine (102) | 33 g/l |
| potassium iodide | 10 g/l |
| 2,3,6-trimethylquinoxaline | 3 g/l |
| sodium 3-nitrobenzenesulphonate | 5 g/l |
| sulphuric acid (96%) | 30 g/l |

EXAMPLE 15

The procedure described in Example 10 is repeated, but instead of the bleaching bath (2), a bath of the following composition is used:

| | |
|---|---|
| sulphamic acid | 140 g/l |
| sodium 3-nitrobenzenesulphonate | 6 g/l |
| 2,3,6-trimethylquinoxaline | 2 g/l |
| potassium iodide | 6 g/l |
| bis-(β-cyanoethyl)-sulphoethylphosphine, sodium salt (formula 101). | 2.5 g/l |

With this composition the bleaching time can be reduced to 3 minutes. Equally good results are obtained with the phosphines of Examples 2 to 9.

We claim:

1. A method of processing imagewise exposed photographic silver dye bleach materials involving the process steps
   (1) silver developing,
   (2) dye bleaching,
   (3) silver bleaching,
   (4) fixing,
it being possible to combine process step (3) with at least one of the process steps (2) and (4) in a single treatment step, which method comprises using in at least one of the steps (2), (3) or (4) a water-soluble tertiary phosphine of the formula

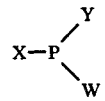

is used as silver ligand, wherein W is a radical of the formula $-C_rH_{2r}CN$ or $-C_2H_{2r}NO_2$, in which r is an integer from 1 to 25, a pyridine, pyrazine or triazine radical or a radical of the formulae

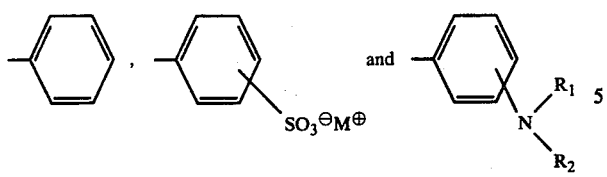 and wherein $M^{\oplus}$ is a cation and each of $R_1$ and $R_2$ is independently a hydrogen atom or an alkyl group of 1 to 4 carbon atoms, X is $-(CH_2-CH_2O)_n-R_3$, -alkyl-$SO_3^{\ominus}M^{\oplus}$, -alkyl-$SO_2$—U, -alkyl-$PO_3^{\ominus\ominus}M^{\oplus}M^{\oplus}$, -alkyl-CO—O—$R_3$, -alkyl-CO—N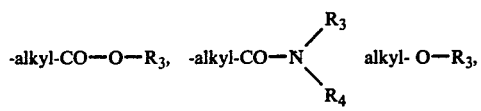 alkyl- O—$R_3$, -alkyl-O—OC—$R_3$, -alkyl-CN, -alkyl-$NO_2$,

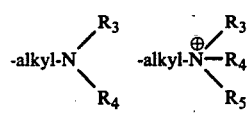

or alkyl-halogen, wherein the alkyl moiety contains 1 to 15 carbon atoms, $M^{\oplus}$ is a cation, each of $R_3$, $R_4$ and $R_5$ is independently a hydrogen atom or an alkyl group of 1 to 4 carbon atoms, U is an alkyl group of 1 to 4 carbon atoms and n is an integer from 1 to 5, and Y is a radical of the formula $-C_rH_{2r}SO_3^{\ominus}M^{\oplus}$, $-C_rH_{2r}-O-R_1$, $-(CH_2-CH_2-O)_{\overline{n}}R_1$, $-C_rH_{2r}-N\overset{T_1}{\underset{Q_1}{\diagup}}$,

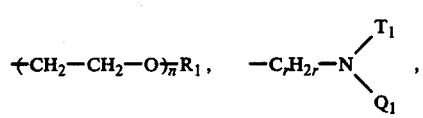

wherein n is an integer from 2 to 5, r is an integer of 1 to 25 and $M^{\oplus}$ is a cation, each of $R_1$, $Q_1$ and $T_1$ is independently a hydrogen atom or an alkyl group of 1 to 4 carbon atoms, $Q_1$ and $T_1$ together with the nitrogen atom to which they are attached can also form one of the radicals of the formulae

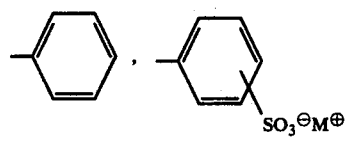

and X and Y together are $-CH_2-CH_2-NR_1-CH_2-CH_2-$, wherein $R_1$ has the indicated meaning.

2. A method according to claim 1 wherein the silver ligand is a phosphine of the formula

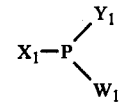

wherein $W_1$ and $X_1$ are as defined in claim 3 and $Y_1$ is $-C_{r_1}H_{2r_1}SO_3^{\ominus}M^{\oplus}$, $-C_{r_1}H_{2r_1}-O-R_1$, $-(CH_2-CH_2-O)_{\overline{n}}R_1$, $C_{r_1}H_{2r_1}-N\overset{T_1}{\underset{Q_1}{\diagup}}$,

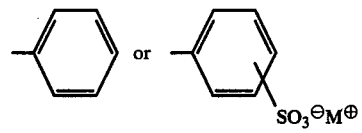

wherein n is an integer from 2 to 4, $r_1$ is an integer from 1 to 15 and $M^{\oplus}$ is a cation and each of $R_1$, $Q_1$ and $T_1$ independently represents a hydrogen atom or an alkyl group of 1 to 4 carbon atoms, $Q_1$ and $T_1$ together can be a radical of the formula

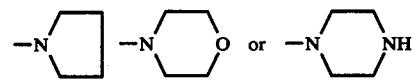

and $X_1$ and $Y_1$ together with the nitrogen atom to which they are attached can be $-CH_2-CH_2-NR_1-CH_2-CH_2-$, wherein $R_1$ has the indicated meaning.

3. A method according to claim 1, wherein the silver ligand is a phosphine of the formula

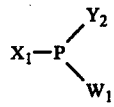 (5)

wherein $W_1$ and $X_1$ are as defined in claim 1 and $Y_2$ is $-C_{r_2}H_{2r_2}-SO_3^{\ominus}M^{\oplus}$, $-(CH_2-CH_2-O)_{\overline{n_1}}R_1$, $-C_{r_2}H_{2r_2}-N\overset{T_1}{\underset{Q_1}{\diagup}}$ or 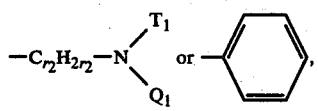, wherein $n_1$ is an integer from 1 to 3, $r_2$ is an integer from 1 to 4 and $M^{\oplus}$ is a cation, each of $R_1$, $Q_1$ and $T_1$ independently is a hydrogen atom or an alkyl group of 1 to 4 carbon atoms, $Q_1$ and $T_1$ together with the nitrogen atom to which they are attached can be a radical of the formula

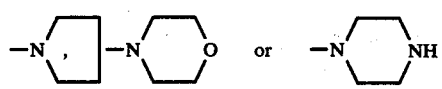

and $X_1$ and $Y_2$ together can be $-CH_2-CH_2-NR_1-CH_2-CH_2-$, wherein $R_1$ has the indicated meaning.

4. A process according to claim 3, wherein the silver ligand is a phosphine of the formula $$X_1-P\begin{matrix}Y_3\\ W_1\end{matrix},$$

wherein $W_1$ and $X_1$ are as defined in claim 1 and $Y_3$ is

—$(CH_2)_2$—$SO_3^{\ominus}M^{\oplus}$, —$(CH_2)_3$—$SO_3^{\ominus}M^{\oplus}$,

—$(CH_2)_4$—$SO_3^{\ominus}M^{\oplus}$, —$\underset{\underset{CH_3}{|}}{CH}(CH_2)_2SO_3^{\ominus}M^{\oplus}$,

—$CH_2$—$CH_2$—O—$CH_3$, —$CH_2N(CH_3)_2$, —$CH_2$—$N(C_2H_5)_2$,

—$(CH_2)_2$—$N(CH_3)_2$, —$(CH_2)_3$—$N(CH_3)_2$,

—$(CH_2)_2$—$N(C_2H_5)_2$, —$(CH_2)_3$—$N(C_2H_5)_2$,

—$(CH_2)_2$—N⟨pyrrolidinyl⟩,

—$(CH_2)_3$—N⟨pyrrolidinyl⟩,

—$(CH_2)_2$—N⟨morpholinyl⟩O,

—$(CH_2)_3$—N⟨morpholinyl⟩O,

—$(CH_2)_2$—N⟨piperazinyl⟩NH or

—$(CH_2)_3$—N⟨piperazinyl⟩NH , wherein $M^{\oplus}$ is a cation and $X_1$ and $Y_3$ together can be —$CH_2$—$CH_2$—$NR_1$—$CH_2$—$CH_2$—, wherein $R_1$ has the indicated meaning.

5. A method according to claim 4, wherein the silver ligand is a phosphine of the formula $$X_2-P\begin{matrix}Y_3\\ W_2\end{matrix},$$

wherein $Y_3$ is as defined in claim 6, $W_2$ is —$CH_2$—$CH_2$—CN,

[phenyl] or [phenyl-$SO_3^{\ominus}M^{\oplus}$]

and $X_2$ is

—$(CH_2$—$CH_2O)_nR_1$, —alkyl—$SO_3^{\ominus}M^{\oplus}$, —alkyl—CO—O—$R_1$,

-continued

—alkyl—CO—N⟨$R_1$,$R_2$⟩, —alkyl—O—$R_1$,

—alkyl—CN oder —alkyl—hydrogen, wherein each of $R_1$ and $R_2$ independently is a hydrogen atom or an alkyl group of 1 to 4 carbon atoms, alkyl is an alkylene group of 1 to 4 carbon atoms, n is an integer from 1 to 5, $M^{\oplus}$ is a cation and halogen is in particular a chlorine or bromine atom, and $X_2$ and $Y_3$ together can be —$CH_2$—$CH_2$—$NR_1$—$CH_2$—$CH_2$—, wherein $R_1$ has the indicated meaning.

6. A method according to claim 5, wherein the silver ligand is a phosphine of the formula $$X_3-P\begin{matrix}Y_3\\ W_3\end{matrix},$$

wherein $Y_3$ is as defined in claim 6, $W_3$ is —$CH_2$—$CH_2$—CN or

[phenyl] and $X_3$ is —$(CH_2)_k$—$SO_3^{\ominus}M^{\oplus}$,

—$(CH_2)_{\overline{n}}OR_1$—$\underset{\underset{U}{|}}{CH}$—$CH_2$—$CH_2$—$SO_3^{\ominus}M^{\oplus}$, $(CH_2$—$CH_2O)_{\overline{n_1}}R_2$, wherein $M^{\oplus}$ is a cation, U is an alkyl group of 1 to 4 carbon atoms, $n_1$ is a integer from 2 or 3 and k is an integer from 2 to 4, $R_1$ and $R_2$ are as defined in claim 7 and $X_3$ and $Y_3$ together can be —$(CH_2)_2$—$N(CH_3)(CH_2)_2$—.

7. A method according to claim 6, wherein the silver ligand is a phosphine of the formula $$X_4-P\begin{matrix}Y_3\\ W_3\end{matrix},$$

wherein $W_3$ and $Y_3$ are as defined in claim 6 and $X_4$ is

—$CH_2$—$CH_2$—CN, —$(CH_2)_2$—$SO_3^{\ominus}M^{\oplus}$,

—$(CH_2)_3$—$SO_3^{\ominus}M^{\oplus}$, $(CH_2)_4$—$SO_3^{\ominus}M^{\oplus}$, $\underset{H_3C}{\diagdown}$CH—$CH_2$—$CH_2$—$SO_3^{\ominus}M^{\oplus}$, —$(CH_2)_2$—O—$CH_3$ or —$(CH_2)_2$—O—$(CH_2)_2$—O—$CH_3$, wherein $M^{\oplus}$ is a cation and $X_4$ and $Y_3$ together can be —$(CH_2)_2$—$N(CH_3)$—$(CH_2)_2$—.

8. A method according to claim 7, wherein the silver ligand is a phosphine of the formula

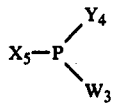

wherein $W_3$ is as defined in claim 6, $Y_4$ is $-(CH_2)_2-SO_3 {}^\ominus M^\oplus$, $-(CH_2)_3-SO_3 {}^\ominus M^\oplus$, $-(CH_2)_4-SO_3 {}^\ominus M^\oplus$, $-CH_2N(C_2H_5)_2$ or $-(CH_2)_2-OCH_3$, $X_5-CH_2-CH_2-CN$ or $-(CH_2)_2-OCH_3$ and $M^\oplus$ is a cation and $X_5$ and $Y_4$ together can be $-(CH_2)_2-N(CH_3)(CH_2)_2-$.

9. A method according to claim 1, wherein a preparation which contains
   (a) a strong acid,
   (b) a water-soluble iodide,
   (c) a dye bleach catalyst in an amount of 0.5 to 5 g/l,
   (d) an organic water-soluble oxidant,
   (e) an antioxidant, and
   (f) a water-soluble tertiary phosphine,
is used for the silver bleaching (3), optionally combined with the dye bleaching (2).

10. A method according to claim 1, wherein a bleach-fixing preparation which contains
    (a) a strong acid,
    (b) an organic water-soluble oxidant,
    (c) one or more of the ligands: thiocyanide, chloride, bromide, iodide and thiourea,
    (d) optionally a dye bleach catalyst, and
    (e) a water-soluble tertiary phosphine,
is used for the silver bleaching (3) combined with the fixing (4).

11. A method according to claim 1, wherein a preparation which contains
    (a) a strong acid,
    (b) a water-soluble organic oxidant,
    (c) a catalyst,
    (d) optionally a water-soluble iodide, and
    (e) a water-soluble tertiary phosphine,
is used for simultaneously carrying out the process steps dye bleaching (2), silver bleaching (3) and fixing (4).

12. A method according to claim 1, in which a photographic material is used which contains, in each of at least two layers, a dye which can be bleached imagewise and whose absorption maximum corresponds to one of the primary colours red, green and blue, with a silver halide emulsion layer sensitive to a particular spectral region being assigned to each dye, and in this material,
    (a) a silver halide emulsion layer consisting at least partially of silver iodide is assigned to the dye whose undesired parasitic colour density is to be compensated,
    (b) in a further layer, at least a second dye whose main colour density corresponds to a parasitic colour density, requiring compensation, of the first dye and a silver halide emulsion which contains no iodide ions are present,
    (c) a further layer, which is adjacent to the layer containing the second dye, contains colloidal nuclei which are capable of depositing metallic silver from soluble silver complexes,
    (d) a separating layer is present between the layer containing the nuclei and the dye layer the parasitic colour density of which is to be compensated, and the silver developing bath with which the material is treated contains a ligand which is able to produce water-soluble silver complexes which are capable of diffusion, wherein at least one processing bath contains water-soluble tertiary phosphine.

13. A process of claim 8 wherein the silver ligand is a phosphine of the formula

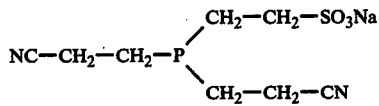

14. Preparation suitable for carrying out the processing method according to claim 1, which contains as silver ligand a water-soluble tertiary organic phosphine in solution.

* * * * *

UNITED STATES PATENT AND TRADEMARK OFFICE
CERTIFICATE OF CORRECTION

PATENT NO. : 4,138,256

DATED : February 6, 1979

INVENTOR(S) : Christoph Chylewski et al.

It is certified that error appears in the above-identified patent and that said Letters Patent are hereby corrected as shown below:

Column 1, line 54, "bleaching" should be --bleach--.

Column 1, line 54, "mixing" should be --fixing--.

Column 3, line 12, "n" should be --N--.

Column 3, line 33, "$K^B$" should be --$K^{\oplus}$--.

Column 7, line 53, "$CH_2CN$" should be --$CH_2$-CN--.

Column 13, line 39, "ioxide" should be --iodide--.

Column 17, line 21, "The" should be --A--.

UNITED STATES PATENT AND TRADEMARK OFFICE
CERTIFICATE OF CORRECTION

PATENT NO. : 4,138,256
DATED : February 6, 1979
INVENTOR(S) : Christoph Chylewski et al.

It is certified that error appears in the above–identified patent and that said Letters Patent are hereby corrected as shown below:

Column 22, line 7, "Claim 3" should be --claim 1--.
Column 22, line 36, "1" should be --2--.

Column 24, line 24, "claim 6" should be --claim 4--.
Column 23, line 57, "claim 6" should be --claim 4--.

Signed and Sealed this

Third Day of July 1979

[SEAL]

Attest:

LUTRELLE F. PARKER
*Attesting Officer*   *Acting Commissioner of Patents and Trademarks*